(12) United States Patent
Maier et al.

(10) Patent No.: US 8,353,256 B2
(45) Date of Patent: Jan. 15, 2013

(54) INSTALLATION AND DEVICE FOR GUIDING A GAS FOR DEVICES USED TO TREAT GRANULAR PRODUCTS BY DRYING, FILM COATING AND COATING

(75) Inventors: Johann-Georg Maier, Bingen (DE); Dietmar Hiller, Kirchdorf (DE); Frank Sauter, Oberstadion-Hundersingen (DE); Eberhard Jaeger, Erolzheim (DE); Daniel Becker, Assmannshardt (DE); Roland Missel, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1351 days.

(21) Appl. No.: 11/916,714

(22) PCT Filed: Jun. 14, 2006

(86) PCT No.: PCT/EP2006/063227
§ 371 (c)(1),
(2), (4) Date: Mar. 5, 2008

(87) PCT Pub. No.: WO2006/134133
PCT Pub. Date: Dec. 21, 2006

(65) Prior Publication Data
US 2008/0199375 A1 Aug. 21, 2008

(30) Foreign Application Priority Data
Jun. 17, 2005 (DE) .......................... 10 2005 028 168

(51) Int. Cl.
*B05C 11/00* (2006.01)
*D06F 58/00* (2006.01)

(52) U.S. Cl. .......................................... 118/58; 34/134
(58) Field of Classification Search ................ 34/134, 34/131, 607, 520, 63; 159/23
See application file for complete search history.

(56) References Cited

U.S. PATENT DOCUMENTS
532,553 A * 1/1895 Hentschel ...................... 34/138
(Continued)

FOREIGN PATENT DOCUMENTS
EP 0080199 A2 11/1982
(Continued)

OTHER PUBLICATIONS
International Search report of international Application PCT/EP2006/063227.

*Primary Examiner* — Dah-Wei Yuan
*Assistant Examiner* — Charles Capozzi
(74) *Attorney, Agent, or Firm* — Michael P. Morris; Alan R. Stempel

(57) ABSTRACT

An installation for guiding a gas for devices used to treat granular products by drying, film-coating or coating includes: a central distribution channel that can be connected to a gas supplying device and is connected to outlets for the gas, that are arranged at a distance from the central distribution channel in an axial direction, via connection channels. The installation includes a functional channel which is arranged at a distance from the distribution channel and has a plurality of outlets, and the functional channel includes at least two axially interspaced inlet regions, each being connected to the distribution channel via a connection channel. The outlets are arranged, in the axial direction on the functional channel, between the mouth of two connection channels, which are adjacently arranged in the axial direction, in the functional channel.

39 Claims, 9 Drawing Sheets

U.S. PATENT DOCUMENTS

| | | | |
|---|---|---|---|
| 2,892,262 A * | 6/1959 | Shirk | 34/585 |
| 3,302,608 A * | 2/1967 | Coons et al. | 118/19 |
| 3,874,092 A * | 4/1975 | Huttlin | 34/130 |
| 4,563,315 A | 1/1986 | Walter et al. | |
| 6,569,462 B1 | 5/2003 | Cornelli et al. | |
| 6,742,473 B1 * | 6/2004 | Giogoli et al. | 118/19 |
| 2006/0112589 A1 * | 6/2006 | Huttlin | 34/585 |

FOREIGN PATENT DOCUMENTS

| | | |
|---|---|---|
| EP | 0732882 | 9/1996 |
| WO | 9519713 A1 | 7/1995 |
| WO | 0126601 A1 | 4/2001 |
| WO | WO 2004007085 A1 * | 1/2004 |
| WO | 2004093881 A | 11/2004 |

* cited by examiner

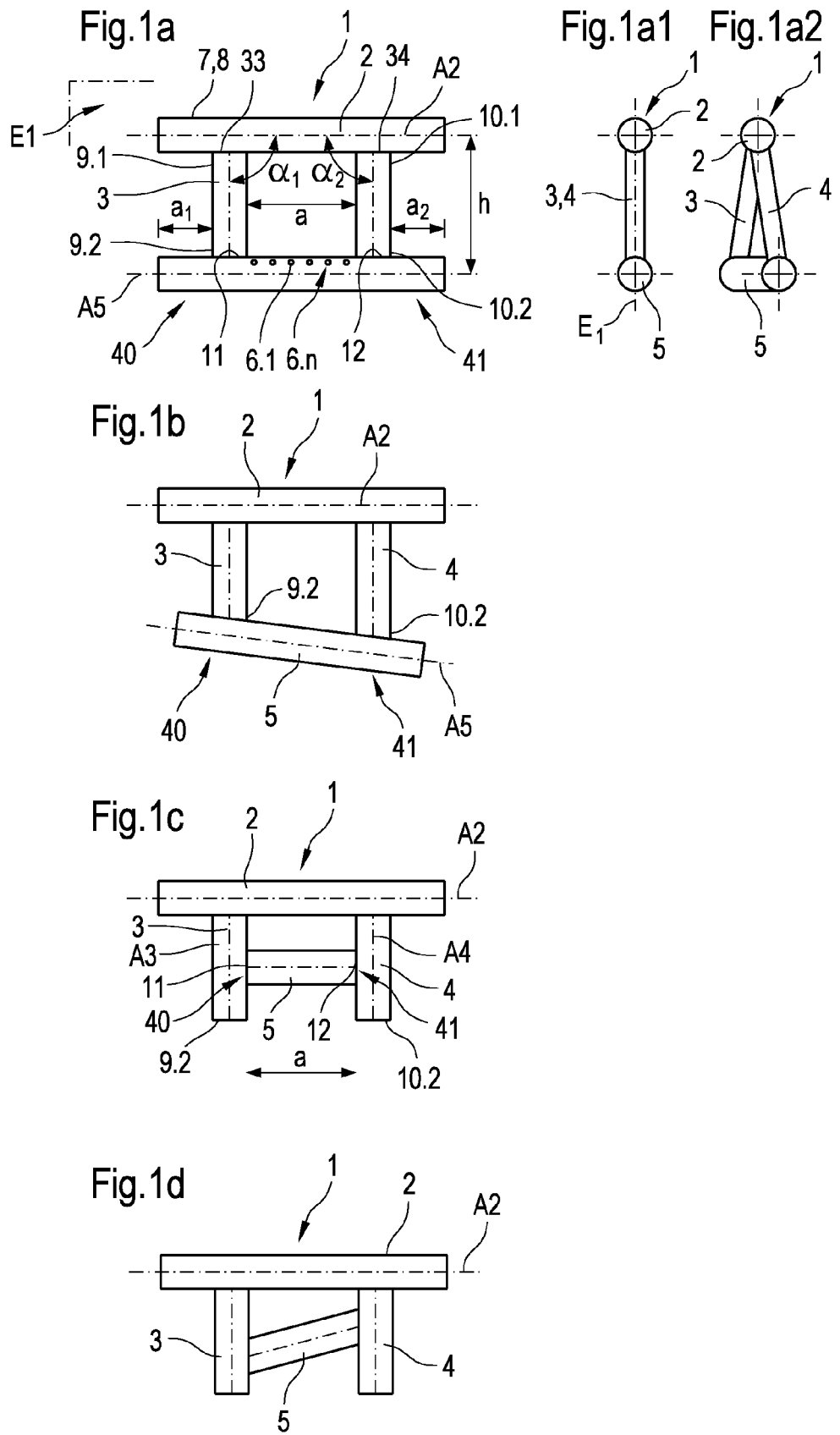

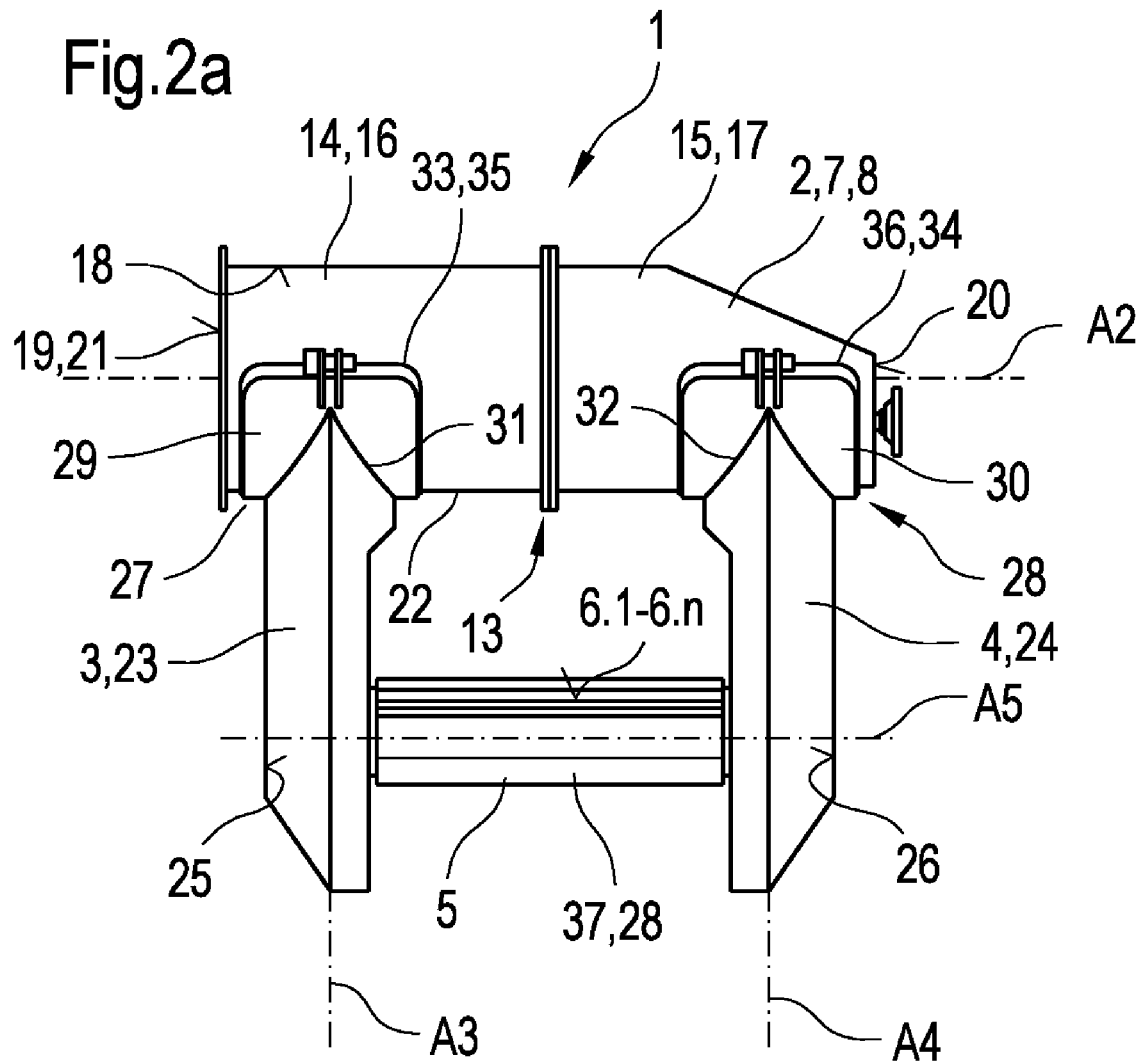
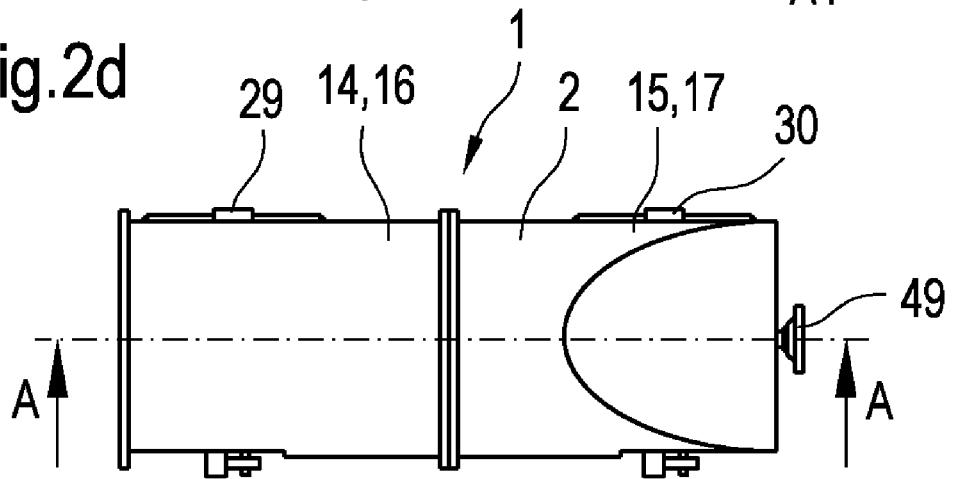

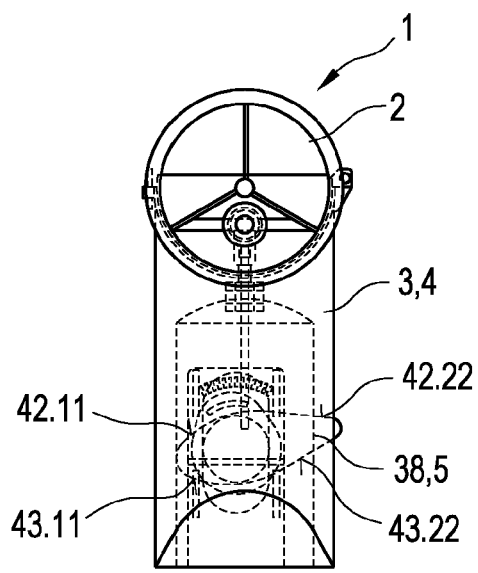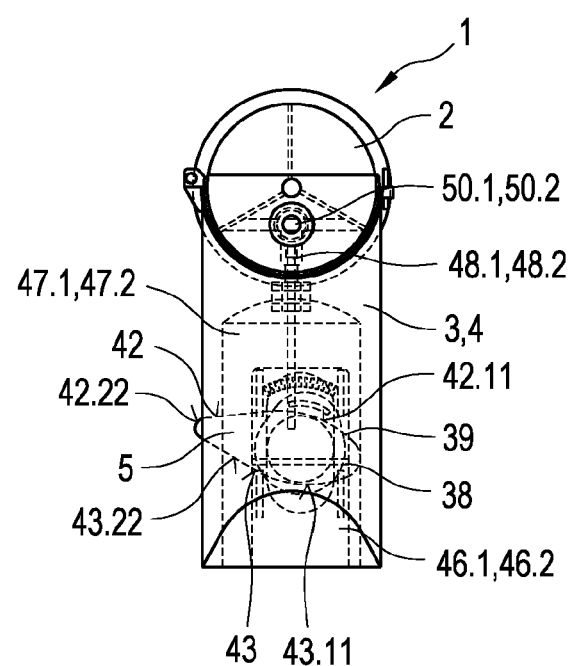

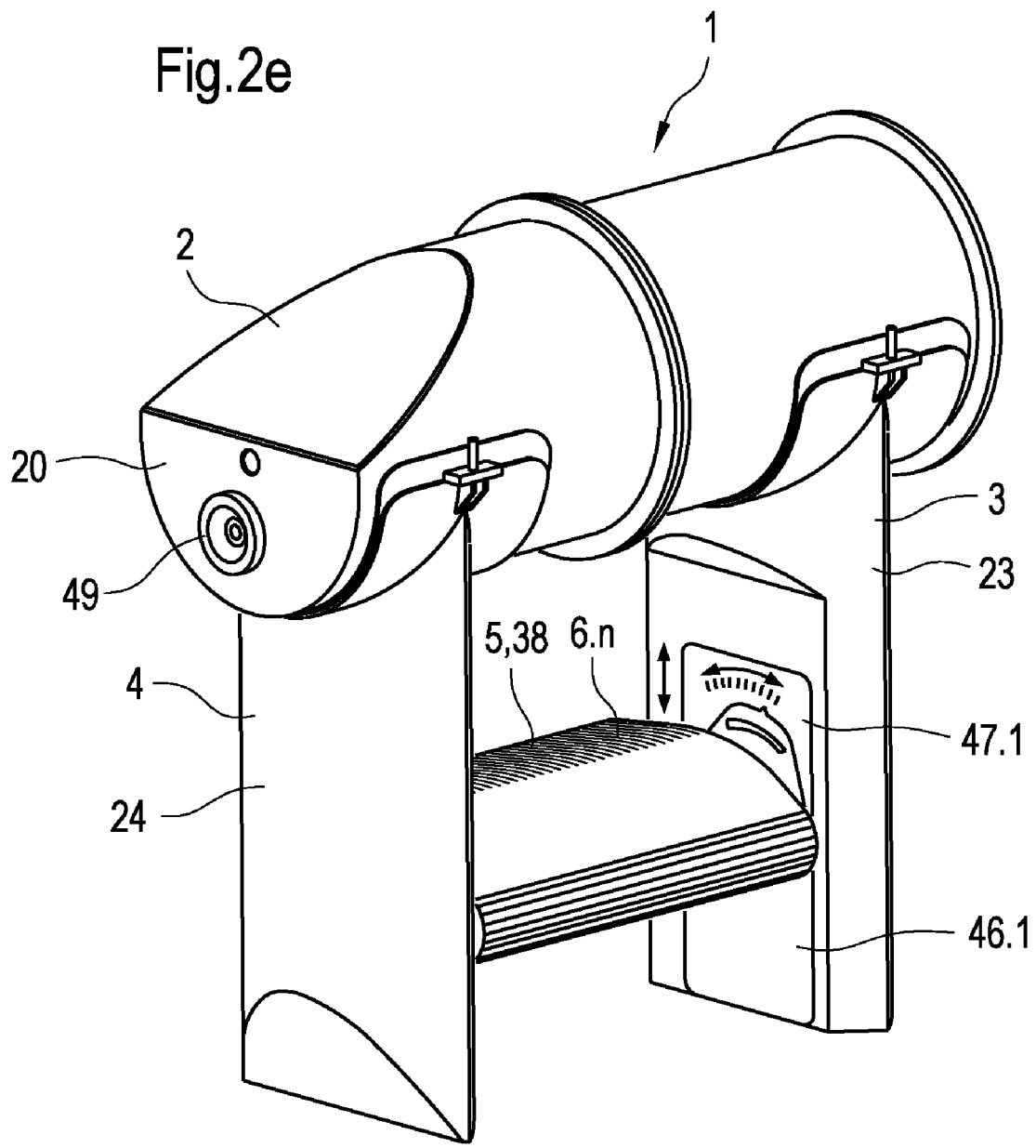

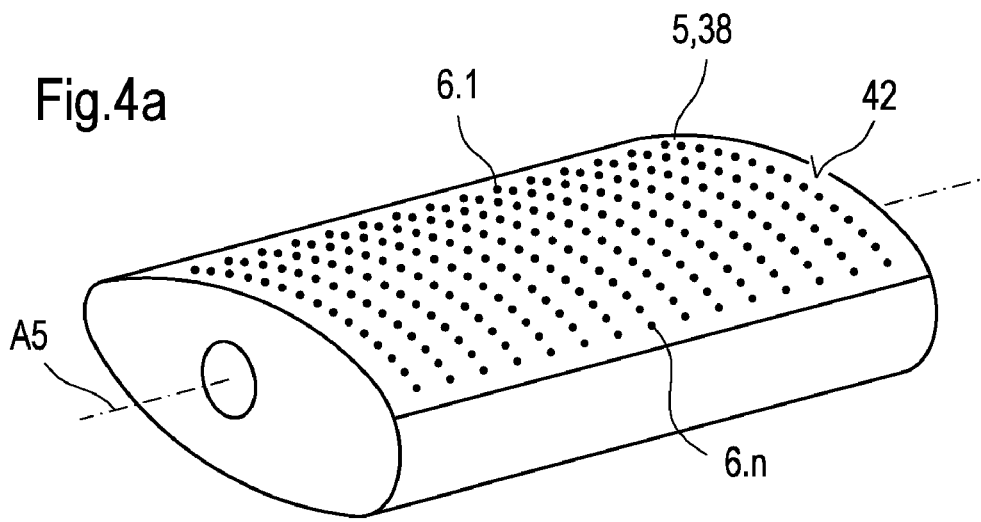
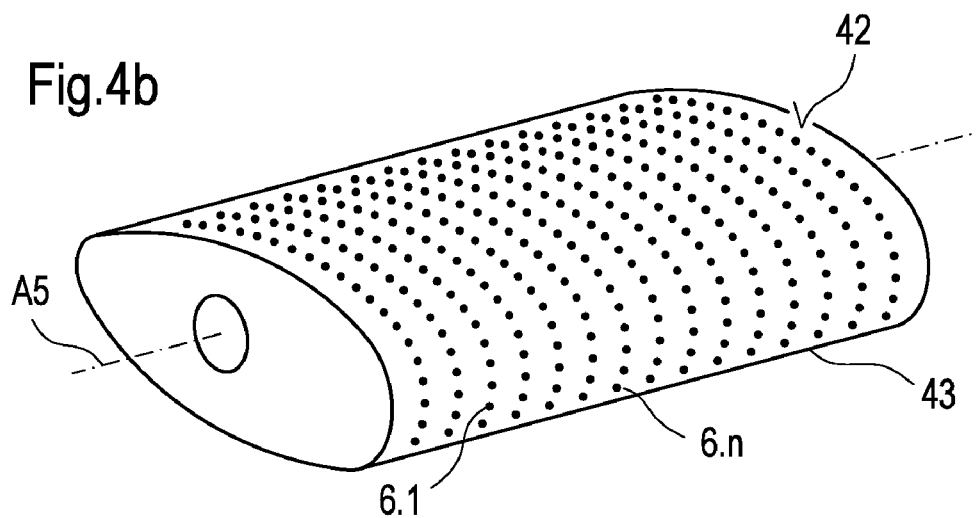
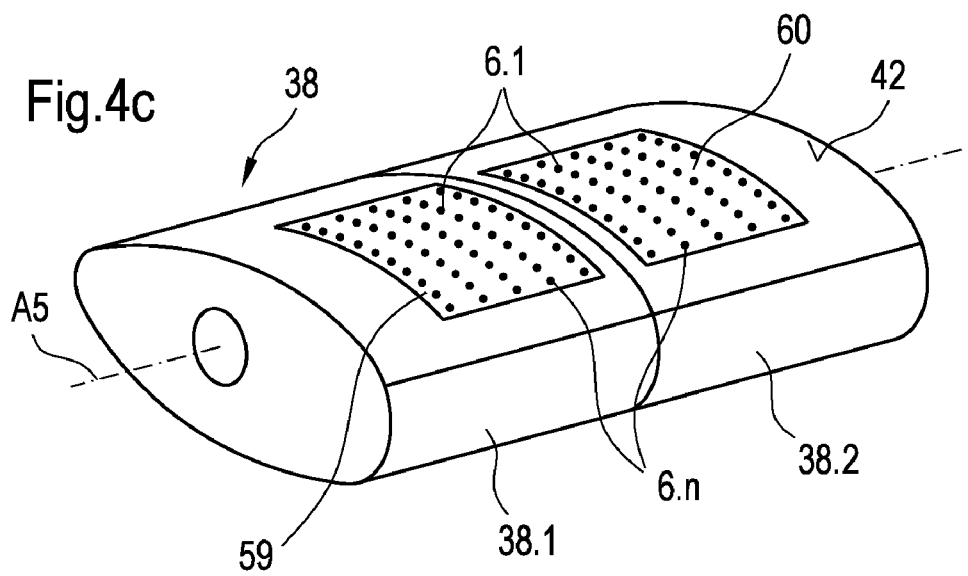

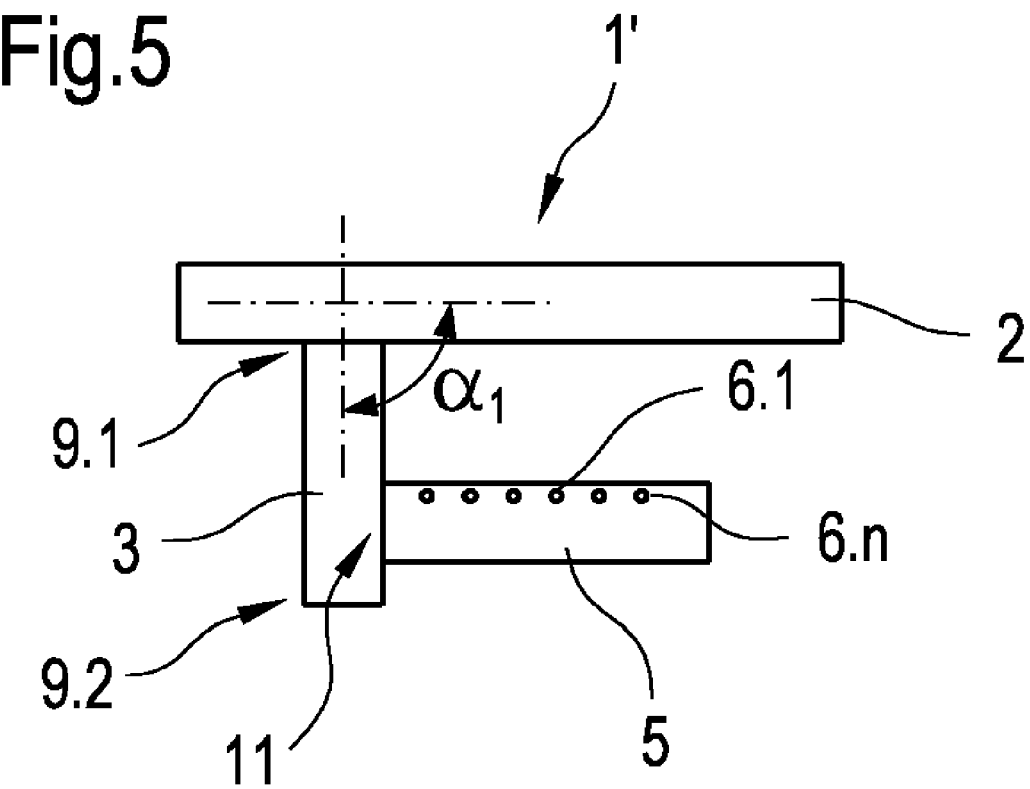

INSTALLATION AND DEVICE FOR GUIDING A GAS FOR DEVICES USED TO TREAT GRANULAR PRODUCTS BY DRYING, FILM COATING AND COATING

FIELD OF THE INVENTION

The invention relates to an installation for guiding a gas for devices used to treat granular products by drying, film-coating or coating, especially an incoming air unit, specifically having the features of a central distribution channel that can be connected to a gas supply device and is connected, via connection channels, to axially spaced outlets for the gas that are spaced from said channel, and also an apparatus for treating granular products by drying, film-coating or coating comprising such an installation, the use of the apparatus for producing dabigatran etexilate pellets or dipyridamole delayed-release forms and the products obtained using the apparatus.

BACKGROUND OF THE INVENTION

Apparatus for treating granular products by drying, film-coating or coating are known in a variety of forms. For a representative sample, reference is made to the following publications:
EP 0 080 199 A2
EP 0 732 882 B1
WO 01/26601

The publication EP 0 080 199 A2 discloses an apparatus for treating granular products by drying, film-coating or coating. It comprises a drum mounted so as to rotate about a horizontal axis, in which inlet and outlet lines for a gas for drying a product contained in the drum are connected to an immersion member that has inlet and outlet openings for the gas and within the drum assumes a position in which it is immersed in the product. The immersion member is in the form of a tunnel through which the product can flow, inside which are provided at least some of the inlet and outlet openings for the gas. The tunnel is aligned in the direction of flow of the product, in the position of installation. If there is product in the drum, moistening medium emerging from a nozzle, for example, is sprayed onto the product from above and below while the drum rotates. The upper layer of product flows downwards at an angle to the horizontal. The immersion member is immersed in this downward flowing layer of product. The immersion member comprises an intermediate base which in cooperation with axial partition walls and partition walls provided in the direction of flow divides it into an annular inlet chamber for drying gas and a flat outlet chamber. The inlet chamber is connected to an inlet line and the outlet chamber is connected to an outline line. The intermediate base has slot-shaped inlet openings that extend over the entire width and open up a path for the drying gas from the inlet chamber into the inner space of the tunnel formed by the immersion member. In this solution the amount of product subjected to direct drying is dependent on the geometry of the tunnel, the depth of immersion and the arrangement of the outlet channels and therefore has to be specifically adapted to each individual case. Moreover, for optimum drying, it is necessary to ensure on the one hand an internal width of the inlet cross section depending on the width of the drum and furthermore a specific predefined level of filling of the drum, which in the position of installation of the immersion member always guarantees that it is filled between the intermediate base and intermediate ceiling. The product is dried from below, which can lead to unsatisfactory and uneven drying results if the fill level is high and there is a correspondingly great tunnel height. Admittedly, the slot-like design of the outlet openings for the drying gas ensure direct drying over a fairly large area in the direction of flow, but the entire annular chamber is supplied through only a single inlet chamber. A further disadvantage is the complex geometry of the element that forms the tunnel and carries the outlet openings for the drying gas, which requires specific adaptation to the design of the drum, the lack of exchangeability and lack of adaptability to changing fill levels.

From the publication EP 0 732 882 B1 a design of an apparatus for treating granular products is known which makes it possible to dry granular products in a rotatably mounted coating pan through air outlet means provided with perforated hollow bodies that can be immersed in the product. The outlet openings are arranged on tubular elements that extend radially from a distribution channel and are thus in a fixed position relative to the distribution channel. Depending on the fill level of the drum, different depths of immersion of the air outlet means in the product are provided, that are reflected in different drying results. In addition, because of the radially aligned arrangement of the outlet openings and their cross-sections, the activity and hence drying areas extend only in an annular configuration around them.

To solve the problem, telescope-like hollow bodies are known from WO 01/26601, which are adjustable in length, extend vertically from the distribution channel and can be immersed in the moving mass of the product that is to be treated. In their distal part the hollow bodies have an elongate cross section with pointed ends, that is open at the bottom, forming the outlet openings, and also has perforated areas on the side walls for the exit of the drying gas. The effective drying area can thus be enlarged. However, a disadvantage here is the greatly limited drying area around the outlet openings on the telescopic hollow bodies, extending around the individual hollow bodies, the drying action decreasing in the radial direction.

SUMMARY OF THE INVENTION

The problem which underlies the invention is therefore to further develop an installation for guiding a gas in apparatus for treating granular products such that the disadvantages mentioned above are avoided and, using means that are simple in construction, a large drying area is obtained which is easily accessible for the majority of the product that is to be treated, while the drying intensity should be as uniform as possible irrespective of the fill level of the apparatus. In addition, the solution according to the invention should be characterised by its simple structure and should also be suitable for fitting to existing apparatus.

A solution according to the invention is characterised in accordance with one embodiment by an installation for guiding a gas for apparatus for treating granular products by drying, film-coating or coating, especially an incoming air unit, comprising a central distribution channel that can be connected to a gas supply device and is connected, via connection channels to axially spaced outlets for the gas that are spaced from said channel, having a functional channel that comprises a plurality of outlets and is spaced from the distribution channel, the functional channel comprising at least two inlet regions axially spaced from one another, each of the inlet regions being connected to the distribution channel through a connection channel; wherein the outlets are arranged, viewed in the axial direction at the functional channel, between the mouths of two axially adjacent connection channels into the functional channel.

In accordance with another embodiment an installation for guiding a gas for apparatus for treating granular products by drying, film-coating or coating, especially an incoming air unit, comprises a central distribution channel that can be connected to a gas supply device and is connected, via a connection channel, to axially spaced outlets for the gas that are spaced from said channel, having a functional channel that comprises a plurality of outlets and is spaced from the distribution channel, the functional channel comprising an inlet region connected to the distribution channel through the connection channel, the connection channel and the functional channel being arranged at an angle to one another.

In accordance with a further embodiment, an apparatus for treating granular products with an installation according to the invention for guiding a gas includes an apparatus for treating granular products by drying, film-coating or coating, especially for treating pharmaceutical particles having a drum mounted to be rotatable about an axis and adapted to be filled with the product having an installation mounted in the drum for guiding a gas. Further advantageous embodiments are described in the subsidiary claims.

An installation for guiding a gas for devices used to treat granular products by drying, film-coating or coating, especially an incoming air unit, comprising a central distribution channel that can be connected to a gas supply device and is connected via connection channels to outlets for the gas which are at a spacing therefrom and axially spaced from one another, comprises according to the invention a functional channel comprising a plurality of outlets and spaced from the distribution channel. The functional channel comprises according to a first proposed solution at least two inlet regions axially spaced from one another, each of the inlet regions being connected to the distribution channel through a connecting channel. The outlets are arranged between the mouths of two axially adjacent connection channels in the functional channel, viewed in the axial direction at the functional channel.

The term channel is to be understood functionally as being a flow-carrying unit, without any restrictions whatsoever as to its construction and geometry. The individual channel may be formed by a hollow body, incorporated in an element or formed by pipe elements.

According to a second proposed solution the functional channel is connected to the distribution channel through only one connection channel, the functional channel being arranged at an angle to the connection channel and extending away from it. Preferably the functional channel is mounted in an overhung position on the connection channel.

The solution according to the invention thus ensures guidance of the drying air that is characterised by a large radius of activity and also, as a result of the deflection, exits at the desired angle to the product that is to be dried.

The embodiment according to the invention when used in apparatus for treating granular products by drying, film-coating or coating, especially pharmaceutical particles in the form of pellets of granules, for example wherein the elements forming the individual channels are made of metal, plastics or inert material, preferably stainless steel, provides a large area over the width of the apparatus and in the direction of flow, with uniform drying intensity for the product contained in the apparatus, particularly in the rotatable drum and moving over the functional channel during rotation. During the rotation of the drum the product is held in a flowing movement and, depending on the arrangement, a certain layer thickness is guided over the functional channel, while during the downward movement of the product the latter is uniformly exposed to the drying gas coming out of the outlets. The product guided over the functional channel is thus exposed directly to the gas, i.e. dried. There is no need for any guiding of the product beforehand, as in the tunnel solution. The installation according to the invention may be used in apparatus for treating granular products which assume a pure drying function and drying function after coating, active substance spraying or film-coating. For this purpose, coating and/or dampening devices are provided upstream of the apparatus for guiding a gas, in the direction of flow of the product flowing downwards counter to the direction of rotation. The subsequent provision of the apparatus according to the invention has the advantage that after spraying the product is dried in a quasi-fluidised bed, by which is meant a directed and ordered flow in which an increase in volume takes place, as a result of an increase in the average spacing of the particles and hence the surface area that can be exposed to the drying gas, thereby improving the drying performance and reducing the process times.

As well as increasing the drying intensity the solution according to the invention also makes it possible to reduce the process times by shorter heating times and enables the spray rate to be increased without increasing the quantity of air supplied or changing any additional parameters. As a result of the large-area outlet for the drying gas, there is less turbulence in the drum than in the known solutions.

The drying zone formed according to the invention has a length parallel to the rotation axis of the pan which corresponds, for example, to 0.1 to 0.9 times, preferably 0.1 to 0.5 times the width of the drum, particularly in the region of the rotation axis or the functional channel.

The outlets are provided according to the invention on the outer circumference of the functional channel, and are arranged at least on the side or surface directed towards the distribution channel and thus when used in an apparatus for treating granular products are positioned opposite it such that an upper layer of the product is guaranteed to slide down over it.

According to one embodiment, the outlets are also provided on the region of the outer surface of the functional channel directed away from the distribution channel. The advantage of this is that the functional channel can be immersed to any desired depth in the product and because of the escape of drying gas in the opposite direction the drying effect is guaranteed even with different degrees of filling, while fluidisation is also guaranteed in the lower parts of the layer, i.e. those located close to the walls of the drum. This embodiment is particularly advantageous when the position of the functional channel relative to the distribution channel is not changeable.

The outlets cover at least a predefined surface zone on the outer periphery of the functional channel. In order to enlarge the effective outlet cross section the individual outlets are characterised by an outlet cross section in the range from 0.1 to 1 mm, preferably 0.2 to 0.6 mm, especially about 0.5 mm and are arranged at a predefined spacing in the range from 0.5 to 2 mm, preferably 0.8 to 1.5 mm, especially about 1 mm from one another in the axial direction and perpendicularly thereto. Preferably these are formed by close-meshed perforated surface zones, i.e. outlets arranged at very frequent intervals and with a small cross section. The cross-sectional geometry may be circular, polygonal or slot-shaped, for example also honeycomb-shaped. Any other geometry is also possible. The size of the outlet cross section is also dependent on the size of the product that is to be dried.

With regard to the arrangements between at least a partial region of the distribution channel, preferably the whole distribution channel and the functional channel containing the outlet openings a distinction is drawn between the following possibilities:

parallel at an angle to one another.

Preferably, the parallel position is selected, as it allows drying air to act uniformly on the product in the direction of flow and at right angles thereto through the functional channel, when used in apparatus for treating granular products. In addition, this embodiment can also be integrated well into existing apparatus, i.e. it is an easy modification to make, e.g. by replacement. The angular position is only of value when the distribution channel is installed in a corresponding situation, allowing the functional channel to extend axially parallel to the rotation axis of the coating drum in spite of the non-parallel arrangement of the distribution channel. In addition, this position of installation makes it possible to achieve an optimum air guidance in the quasi fluidised bed and to operate with a minimum fill level.

Preferably the distribution channel and connection channels are arranged perpendicularly to one another. This is also analogously true of the functional channel and the connection channels. The arrangement of all of them in a common plane represents an embodiment that is particularly simple to achieve in terms of construction.

Regarding the cross-sectional geometry selected, there are no restrictions on the design of the individual channels. They will be designed as a function of the amount of air supply selected and the desired flow conditions. The functional channel is preferably of wing-like construction, viewed in cross-section, with the aim of reducing the flow resistance, i.e. tilting forward, viewed in the direction of flow of the product. The cross-section is formed by rounded transitions between the upper and lower surfaces joined together, the upper surface and lower surface, viewed in cross section, being characterised by the side-by-side arrangement of surface zones of different configuration and alignment, which slope towards the end zones for the purpose of improving the guiding of the product in the direction of flow.

With regard to the respective positions of the functional and distribution channel, a distinction is drawn between embodiments with a fixed relationship and embodiments that offer the possibility of a change of position. The latter provide the opportunity of optimum adaptation to different levels of fullness, which can be implemented either between different processes or during a process.

Changes in position are produced by a) the possibility of rotating or pivoting the functional channel, for example rotating it about its mounting axis, and/or b) moving it perpendicularly to the distribution channel, i.e. towards or away from it.

The rotatability is most easily achieved by interlockingly or frictionally engaging connecting means between the functional channel and connection channel, with means being provided for securing them. Rotation may take place smoothly or stepwise. In the latter case, the connection means preferably comprise a plurality of engagement means arranged in the circumferential direction of the rotation axis, which are preferably identical in construction and arranged at a certain pitch, i.e. spacing from one another in the circumferential direction which describes the angle of rotation.

In case b) the movement takes place along the longitudinal axes of the connection channels. This may be achieved by various constructions. A distinction is drawn between 1) connection channels of constant length and 2) connection channels of adjustable length.

According to 1), in the simplest case, for this purpose the functional channel is mounted at its end regions in a slide which is in turn guided in a guide on the element forming the connection channel along the longitudinal axis thereof or parallel thereto. Preferably a sliding guide is used, made of Teflon, for example. The slide is preferably constructed so that it covers a larger area in the longitudinal direction than the guide and thus in each functional position there is only a passage between the connection channel and the inlets on the functional channel in the opposing regions on the connection channel and functional channel. Preferably the outlets from the connection channel in the guide region are characterised by a perforated surface on the element that forms the connection channel. Other designs are also possible.

According to 2) the sliding guide may be omitted. The single connection channel is of telescopic construction. By varying the length the functional channel is moved closer to the distribution channel or further away from it.

In both cases, at least one positioning device is provided for carrying out the change of position. It may be integrated in the installation or at least partly arranged outside it. It may be mechanical hydraulic pneumatic electronic a combination of the above solutions.

It may be actuated manually, with servo assistance or automatically. For this purpose a preselection device is provided on which a desired value for a variable that at least indirectly characterises a displacement distance can be preset, and which is connected to a transmission unit that converts the desired value into a set value. According to a solution that can be achieved particularly easily, the transmission unit comprises a gear that converts a rotary movement on the actuating device acting as a preselection device into a longitudinal movement, e.g. in the form of a rack and pinion unit or an angle drive with an internal thread on the driven wheel, that cooperates with an external thread on a rack guided in the driven wheel, the rack being connected to the slide.

As a result of the ways of changing position described, the installation can be operated with different fill levels without affecting the drying results.

The possibility of rotating and moving the functional channel can be implemented with separate positioning means or with one positioning device that performs both functions separately from one another or forcibly coupled together.

The material for the individual elements of the installation is chosen as a function of the demands to be made on the product that is to be treated. Preferably, sheet metal mouldings are used, produced from semifinished sheet metal products by shaping or joining. They are preferably made from stainless steel, because of the exceptional physical and chemical demands.

In the simplest case the connection channel is made from an element that forms a hollow body, which is connected in flow-carrying manner to the distribution channel and the connection channel via opening regions, and extends away from the distribution channel. The distribution channel and the functional channel are preferably formed by a hollow body.

Preferably, the hollow body that forms the functional channel is at least partly formed by a perforated metal sheet, preferably with a support frame or a perforated metal foil. Preferably, inert material is used.

According to another embodiment, the outlets are formed by a perforated metal sheet with a support frame or a perforated metal foil that form part of the outer periphery of the hollow body that describes the functional channel. They are preferably releasably and hence replaceably connected to the hollow body, and cover large opening zones on the outer periphery of the hollow body. This makes removal easy for cleaning purposes or to change the cross-section of passage.

According to a further feature the functional channel is also telescopic in construction. This makes it possible to provide different effective widths to suit different widths of coating devices. It also makes for easy adjustment to different outlet widths at the distribution channel, especially when the installation according to the invention is to be fitted to existing equipment as a modification, using existing distribution channels.

The products to be treated are granular particles, granules or pellets, preferably pharmaceutical products, for example the dabigatran etexilate (ethyl 3-[(2-{[4-(hexyloxycarbonylamino-imino-methyl)-phenylamino]-methyl}-1-methyl-1H-benzimidazole-5-carbonyl)-pyridin-2-yl-amino]-propionate) pellets described in WO 03/074056, or the delayed-release dipyridamole forms described in EP 0032562, which are an ingredient of the preparations Asasantin® and Aggrenox®.

The present invention also relates to the use of the apparatus according to the invention for producing dabigatran etexilate pellets and delayed-release dipyridamole forms and these products prepared using the apparatus according to the invention.

Air is preferably used as the drying gas.

BRIEF DESCRIPTION OF THE DRAWINGS

The solution according to the invention is hereinafter illustrated by means of Figures. These specifically show:

FIGS. 1a to 1d show in schematically simplified representation theoretically possible basic embodiments of installations configured according to the invention;

FIGS. 2a to 2e show an embodiment of an installation according to FIG. 1c in several views;

FIGS. 4a, 4b and 4c show possible arrangements of the outlet openings on the functional channel and FIG. 5 is a highly schematic representation of the basic structure of an installation according to the second proposed solution.

DETAILED DESCRIPTION OF THE INVENTION

Figure 2F:
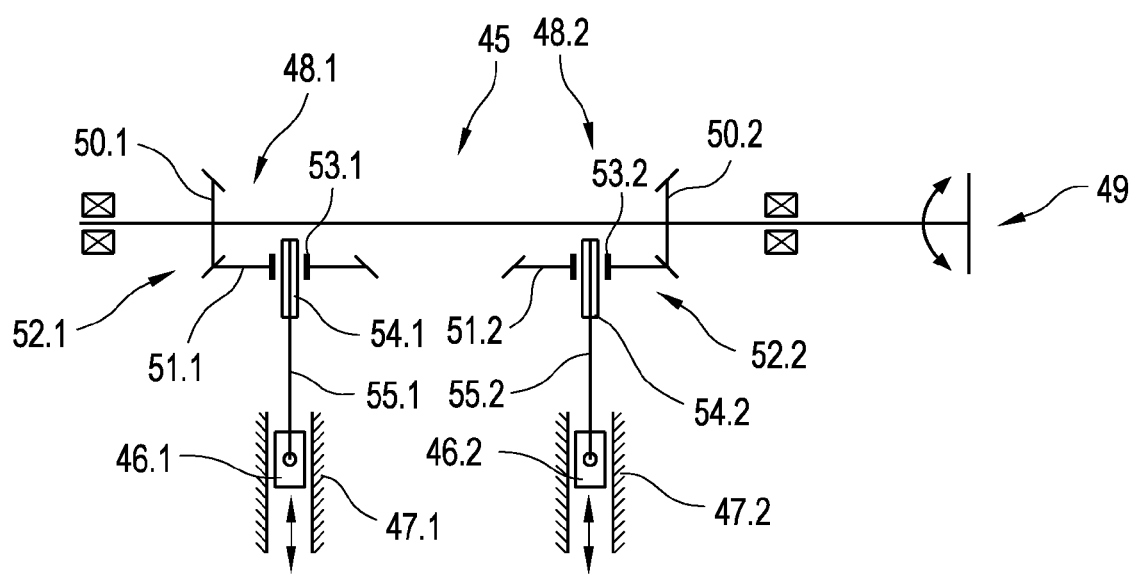
FIG. 2f is a schematically simplified representation showing the structure of a mechanical solution for moving the functional channel.

FIGS. 1a to 1d are schematically simplified representations showing the basic structure of an installation 1 designed according to the invention for use in apparatus for treating granular products by drying, film-coating or coating, especially for apparatus for treating pharmaceutical particles. The apparatus comprises a central distribution channel 2, which can be connected to an incoming air supply unit (not shown here) when used in the apparatus mentioned hereinbefore and from which at least two connection channels 3 and 4 extend, spaced apart from one another at an angle α1 and α2 when viewed in the axial direction. A convergence channel is provided that acts as an actual functional channel 5 in the form of the outlet channel, that is spaced from the distribution channel 2 and is connected to the two axially spaced connection channels 3 and 4 arranged adjacent to one another and thus joins them together. It has at least two inlet regions 11 and 12 and a plurality of outlet openings 6.1 to 6.n for the incoming air entering it through the channels 3 and 4. In accordance with the arrangement and coupling of the individual channels with one another it is possible to distinguish a number of basic variants. All the variants can be configured with a fixed relationship regarding the position between the distribution channel 2 and the functional channel 5 or with a variable arrangement. Changes in the relationship are essentially characterised by the possibility of rotating the functional channel 5 about its axis A5, especially its bearing axis, and/or mobility relative to the distribution channel 2 by varying the distance h in the vertical direction to the distribution channel 2. In all the embodiments there are no restrictions on the selected cross-sectional geometries of the individual channels 3, 4 and distribution channel 2 and functional channel 5. FIGS. 1a to 1c illustrate the possible relationships and connections purely theoretically and schematically. There is no representation of the construction of the elements that form or support the individual channels, namely the distribution channel 2, connection channel 3, 4 and functional channel 5. Moreover, the cross sections of the individual channels shown are purely by way of example. The distribution channel 2 is closed at its end 20 remote from the end that is connected to the incoming air supply unit.

FIG. 1a shows a first embodiment with two views of a functional channel 5 arranged parallel to the distribution channel 2 and comprising outlet openings 6.1 to 6.n. The distribution channel 2 is formed by a hollow body 7, most simply a tubular element 8 of any desired cross-sectional design. This preferably runs axially and has at least two axially spaced outlets 33, 34 for the incoming air. The outlets 33 and 34 are present in the form of openings or a perforated region. The functional channel 5 is arranged at a spacing h from the distribution channel 2. The spacing h corresponds to the spacing in the vertical direction in the position shown, and to the spacing in the radial direction in the mounted position of the installation 1. The outlets 33 and 34 are connected to the functional channel 5 through so-called connection channels 3, 4. These extend away from the distribution channel 2, being arranged adjacent to one another and spaced apart from one another in the axial direction. The connection channels 3 and 4 extend at an angle α1 and α2, preferably at the same angle, preferably an angle of 90°, to the longitudinal axis A2 that describes the extent of the distribution channel 2 in the axial direction. The two connection channels 3 and 4 are preferably arranged parallel to each other. They are each connected to the distribution channel 2 at their first end region 9.1 for the channel 3 and 10.1 for the channel 4, while the second end region 9.2 or 10.2 is connected to the functional channel 5. In the embodiment shown in FIG. 1a, according to FIG. 1a1 the single connection channel 3 or 4 opens perpendicularly into the distribution channel 2 and also perpendicularly into the functional channel 5. All the channels 2, 3, 4 and 5 are arranged in a plane E1. It is also possible for them to open out at an angle, as shown by way of example in FIG. 1a2.

The functional channel 5 viewed in the axial direction extends at least over the spacing a between the two connection channels 3 and 4. In the case illustrated, the functional channel 5 extends over a distance a1 and a2 in the axial direction beyond the spacing a between the two channels 3 and 4 and the widths of the connection channels 3 and 4. The distances a1 and a2 may, however, theoretically also be 0 or may be such that the functional channel 5 terminates flush with the connection channels 3 and 4 in the axial direction. In this case the functional channel 5 is characterised at least by the provision of outlet openings 6.1 to 6.n between the two connection channels 3 and 4, preferably also in the region of the distances a1 and a2.

The two connection channels 3 and 4 or the longitudinal axes A3 and A4 that characterise them and the axis A2 are preferably arranged in a plane E1. This means that the channels 3 and 4 are arranged in the direction perpendicular to the axial direction free from any offset relative to one another, as shown in the view from the right in FIG. 1a1. However, it is also possible for the functional channel 5 to be arranged in a plane parallel to the distribution channel 2, but offset relative thereto with a theoretical projection into a common plane at an angle to one another and hence with a different alignment of the connection channels 3 and 4.

By contrast, FIG. 1b shows an embodiment according to FIG. 1a with a sloping arrangement between the distribution channel 2 and functional channel 5, produced by the angular position of the longitudinal axes A2 of distribution channel 2 and A5 of functional channel 5 to one another. Here again, the attachment to the connection channels 3 and 4 is made in the end regions 9.2 and 10.2. Preferably, here too the connection channels 3 and 4 are also arranged in the direction perpendicular to the axial direction, free from any offset relative to one another, i.e. in one plane.

In the two embodiments according to FIGS. 1a and 1b the functional channel 5 may be connected to the connection channels 3 and 4 with its inlet regions 11 and 12 in the end region 40, 41 or the channels 3 and 4 may open into them at any desired point between the two end regions 40, 41, which will then be closed off. A change of position between the distribution channel 2 and functional channel 5 occurs in the embodiments shown in FIGS. 1a and 1b primarily only if the elements that form the connection channels 3 and 4 and hence the connection channels 3 and 4 themselves are telescopic.

FIG. 1c shows a particularly advantageous embodiment of an installation 1, which is characterised by a constructionally simple structure and easily achievable possibilities for changing the position of the functional channel 5 relative to the distribution channel 2. The distribution channel 2 extends along the longitudinal axis A2 and the two connection channels 3 and 4 extend parallel and axially spaced from one another, forming a spacing a. The longitudinal axis A2 that characterises the distribution channel 2 and the longitudinal axes A3, A4 that describe the path of the connection channels 3 and 4 are preferably arranged in a plane E1. This means that the arrangement of the connection channels 3 and 4 is at the same angle α1 and α2 relative to the longitudinal axis A2 of the distribution channel 2. However, by contrast to the embodiments in FIGS. 1a and 1b, the functional channel 5 is not joined on at the end region 9.2 or 10.2 of the connection channels 3 and 4, but instead the connection channels 3 and 4 are constructed as blind channels, i.e. they are closed off at the end regions 9.2 and 10.2. The functional channel 5 is attached in the region of the extent of the connection channels 3 and 4 perpendicularly to the axial direction, i.e. between the connection channels 3 and 4. The axial extension of the functional channel 5 corresponds substantially to the axial spacing a of the two channels 3 and 4 from one another. In this embodiment the functional channel 5 opens directly with its inlet regions 11 and 12, which are mounted at the ends 40 and 41, into the connection channels 3 and 4. Possible methods of changing the position of the functional channel 5 relative to the distribution channel 2 consist in changing the spacing and/or rotating the functional channel 5 and hence the outlet openings 6.1 to 6.n.

FIG. 1d shows an embodiment according to FIG. 1c with a sloping arrangement of the functional channel 5 relative to the distribution channel 2.

FIGS. 2a to 2e show, in a schematically simplified representation, a number of views of an embodiment of an installation 1 according to the invention as shown in FIG. 1c. It comprises a distribution channel 2 that is formed by a tubular element 8 with a preferably circular cross section substantially over its axial extent. Other cross-sectional geometries are possible. However, each one is characterised by at least one longitudinal axis A2 which describes the path of the distribution channel 2 in the axial direction. The distribution channel 2 is of sectional construction and in the example shown is formed, for example, by two sections 14 and 15 that can be joined together to form a unit in the shape of the tubular element 8, in the form of a base tube 16 and a top tube 17, which can be joined together, preferably releasably. In the simplest case they are joined by flange couplings 13 and/or simple connecting elements. The distribution channel 2 is then described by the inner wall 18 of the tubular element 8. The tubular element 8 is open at its end face 19 formed by the base tube 16 and closed at its end face 20. The opening 21 at the end face 19 can be coupled to other elements of an incoming air supply device, for example other tubular elements for guiding the incoming air and either directly or indirectly via other incoming air supply means with an incoming air supply device. From the outer periphery 22 of the tubular element 8 that forms the distribution channel 2 two connectors 23 and 24 extend, in the form of hollow bodies closed off at one end. They run perpendicularly to the tubular element 8 and contain or form the connection channels 3 and 4; preferably, they are described by the geometry of the inner space 25 and 26 formed by these hollow bodies. The inner spaces 25 and 26 thus formed, which preferably also form or contain the connection channels 3 and 4, are connected, in flow-conducting manner, to the distribution channel 2, and in particular open into the latter. For this purpose, each connector 23 and 24 is constructed, at its end 27 and 28 to be coupled to the distribution channel 2, with a flange 29, 30 adapted to the geometry of the outer periphery 22 of the element 8 that forms the distribution channel 2. The opening 31 or 32 of the connectors in this region then communicates with the distribution channel 2 via openings 33, 34 provided on the element 8 that describes it, the opening 33 describing the region 35 where the connection channel 3 opens into the distribution channel 2 and the opening 34 describing the region 36 where the connection channel 4 opens into the distribution channel 2. The geometry of the connectors, especially the cross-section of the connectors 23 and 24 can take any desired form, the crucial factor being the formation of a connection channel 3 and 4. Preferably the two connectors 23 and 24 are of the same structure and geometry and for the purpose of exchangeability are also symmetrically constructed with respect to the longitudinal axes A3 and A4 that describe the path of the connection channels 3 and 4. The connection channels 3 and 4 are each connected to the functional channel 5 carrying the outlet openings 6.1 to 6.n. This functional channel 5 is also formed by a hollow body 37, which is also referred to as a tongue 38. This is mounted on the two connectors 23 and 24. Preferably so as to be rotatable and movable in the vertical direction. The mounting axis that describes the axis A5 runs parallel to the longitudinal axis A2 of the distribution channel 2 and perpendicularly to the longitudinal axes A3 and A4 of the connection channels 3 and 4.

FIG. 2a shows a view from in front. The parallel arrangement of the connectors 23 and 24 to one another, the parallel arrangement of the tubular element 8 and of the hollow body 37 that forms the functional channel 5, and the structure of the connectors 23 and 24 and the perpendicular arrangement relative to the tubular element 8 and hollow body 37 can be seen. Also shown is the two-part construction of the tubular element 8 and the design of the connections between the individual elements of the tubular element, as well as the tubular element 8 and the connectors 23, 24.

FIGS. 2b and 2c each show a view from the right and left, respectively. They illustrate the arrangement of the distribution channel 2, and of the connection channels 3 and 4 and functional channel 5 in a plane E1. Also shown is the cross-sectional geometry of the drying tongue 38. It is wing-like in design and is characterised by a surface 39 that comprises outlet openings 6.1 to 6.n. The tongue 38 is characterised, in respect of its outer contour, at least by a first upper surface 42 directed towards the distribution channel 2 in the installed position and a second lower surface 43, which is directed away from the distribution channel 2 in the installed position. The outlet openings 6.1 to 6.n may be provided both on the upper surface 42 that is directed towards or points towards the distribution channel 2 in the installed position, and/or on the surface 43 directed away from the distribution channel 2. The single upper surface 42 and the lower surface 43 is characterised by at least two partial surfaces which are adjacent to one another and may be characterised by different geometries and are arranged at an angle to one another or adjacent to one another. In the example shown the tongue 38 preferably has a symmetrical structure relative to a horizontal plane which is characterised by the longitudinal axis A5 and a perpendicular thereto. The individual surfaces 42 and 43 each have two partial surfaces 42.11, 42.22 and 43.11, 43.22. The partial surfaces 42.11 and 43.11 are each curved, when viewed in cross-section, while the partial surfaces 42.22 and 43.22 have a substantially flat configuration, the transition, i.e. the junction between the upper and lower surfaces 42 and 43 being soft, i.e. rounded. At least one partial region of the surfaces—upper and/or lower surface 42, 43—comprises outlet openings 6.1 to 6.n. Also shown is a positioning device 45 for moving the functional channel 5 along the longitudinal axes A3, A4 of the connection channels 3 and 4. The functional channel 5 is mounted at both ends in a slide 46.1, 46.2 for this purpose. This slide is movably guided in a guide 47.1 or 47.2 aligned parallel to the longitudinal axis A3 or A4 of the connection channels 3, 4. The positioning device 45.1 or 45.2 comprises a transmission unit 48.1 or 48.2, which converts the angle of rotation predetermined by an actuating device 49 into an adjusting movement in the longitudinal direction of the axes A3 and A4. The construction and mode of operation are described with reference to a diagram in FIG. 2f.

FIG. 2d shows a perspective view according to FIG. 2a and FIG. 2e shows a view from above, while FIG. 2f shows the method of operation of a mechanical positioning device 45 by way of example.

There are numerous possibilities for achieving rotation and linear movement. In the simplest case, mechanical solutions are used. The drying tongue 38 or the functional channel 5 is rotatably mounted. The mounting is in each case rotational, on a slide 46.1, 46.2 which is movably mounted in a guide 47.1, 47.2 associated with a connector 23 and 24. A rotation angle that corresponds to a displacement distance s is predetermined by the actuating device 49. According to FIG. 2f the desired value $s_{des}$ given as an angle is converted by a transmission unit into the displacement distance s. For this, an angle drive 52.1, 52.2 is provided, the pinions 50.1, 50.2 of which are connected for rotation with the actuating device 49 and mesh with an output gear 51.1, 51.2, the individual output gear being arranged parallel to the longitudinal axis A4, A3 and comprising an internal thread 53.1, 53.2, which cooperates with an external thread 54.1, 54.2 on a connecting element 55.1, 55.2 in the form of a rod. The connecting element 55.1, 55.2 is connected to the slide 46.1, 46.2. The correlation between the rotation angle and displacement distance s is determined by the pitch of the thread.

Figure 3A:
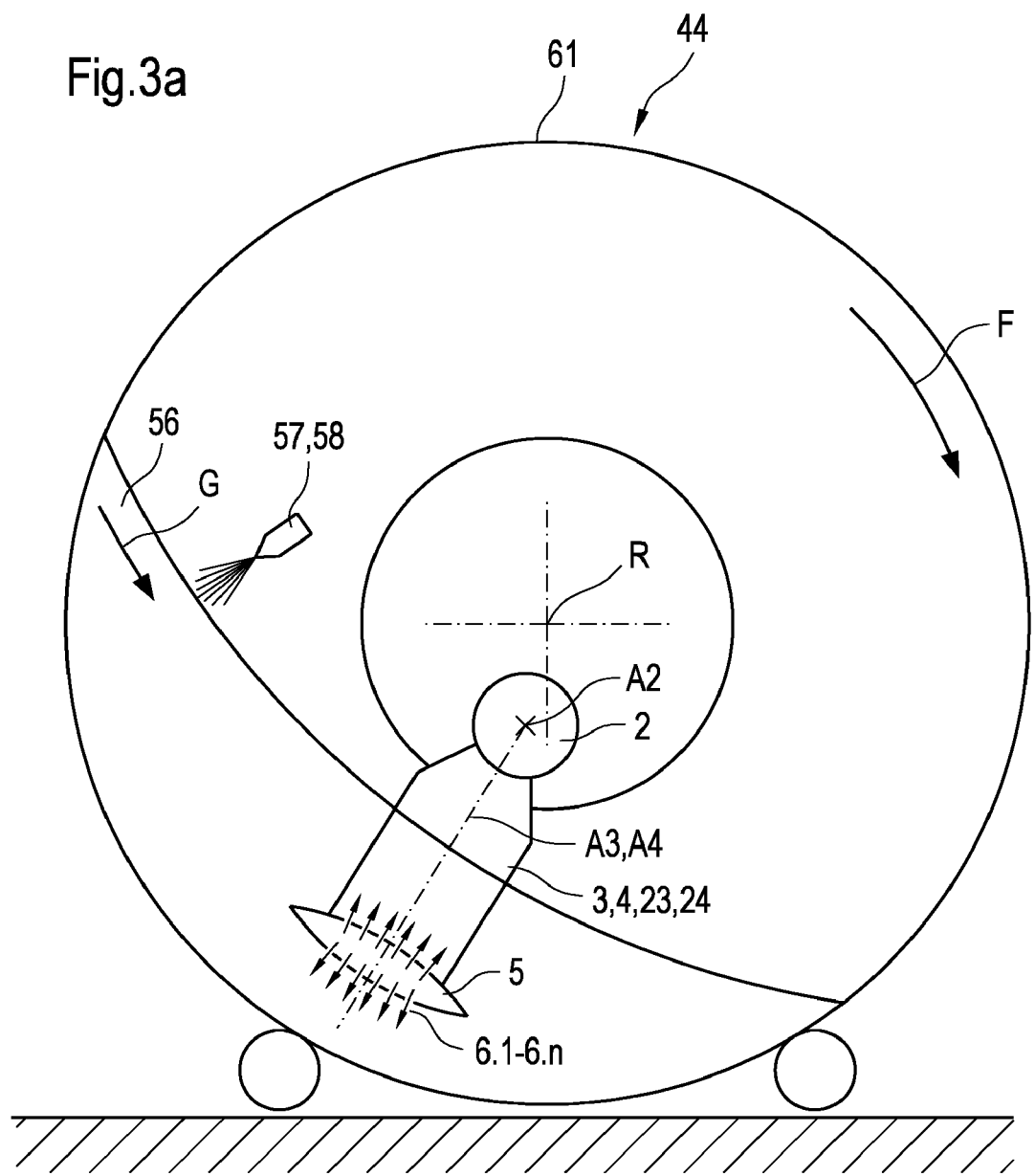
FIGS. 3a and 3b are schematically simplified representations showing the basic structure and operating principle of an apparatus according to the invention for treating granular products.

FIG. 3a illustrates, by means of a highly diagrammatic view, an apparatus 44 constructed according to the invention for treating granular products with an installation 1 according to the invention. The exhaust air guiding means are not shown in this embodiment. These may consist of conventional means, as known from the prior art. The apparatus 44 comprises a drum 61 mounted to be rotatable about a rotation axis R, which contains a predetermined amount of product 56 that is to be treated. The installation 1 is arranged inside the drum 61 parallel to the rotation axis thereof and is connected to a gas providing unit arranged outside the drum 61 and not shown here. The longitudinal axes A2 and A5 of distribution channel 2 and functional channel 5 are also arranged parallel to the rotation axis R. The two connectors 23, 24 which form the connection channels 3 and 4 extend perpendicularly from the distribution channel 2. In the position of installation of the drum 61, the installation 1 is preferably arranged in the lower region, i.e. below a horizontal plane which is characterised by the rotation axis of the drum 61 and a perpendicular thereto in the horizontal direction. An arrangement in the radial direction about the rotation axis R is also possible. The distribution channel 2 is preferably arranged parallel to the rotation axis and either in a vertical plane therewith, with or without an offset in the vertical direction or with an offset in both the vertical and horizontal direction, viewed in the position of installation of the drum 61, opposite it. The connection channels 3 and 4 extend at an angle relative to it and at an angle relative to the vertical plane that can be described by the rotation axis R and a perpendicular in the vertical direction. Preferably, the connection channels 3, 4 extend in a radial direction from the distribution channel 2 and in a radial direction from the rotation axis R towards the inner wall of the drum and allow the functional channel 5 to be immersed or at least operatively connected with the product at its outlets 6.1 to 6.n. Other alignments are possible. The apparatus 44 further comprises an installation 57 for applying a medium to the product 56, especially an installation 57 for moistening, spraying or coating. In the case illustrated, for example, in the form of nozzles 58 that can be coupled outside the drum to corresponding medium supply and guide means (not shown here) extending into the drum 61 and taking the form of either slot-type nozzles or a plurality of individual nozzle elements arranged at an axial spacing from one another. Moistening or coating medium is applied to a top layer of the product 56 from above, by means of the installation 57, while the drum 61 rotates in the direction of the arrow F, carries a lower layer upwards and thus ensures that the upper layer of the product flows downwards in the direction of the arrow G at an angle to the horizontal, preferably at about 45°. The functional channel 5 or the element that forms it is immersed in this downward-flowing top layer of the product 56 and subjects the product 56 to drying gas, preferably drying air, through the outlets 6.1 to 6.n. The functional channel 5 is provided downstream of the installation 57.

FIG. 3a shows the principle of activity of an embodiment with outlets 6.1 to 6.n arranged on both sides of the functional channel 5, as shown by way of example in FIG. 4b. The functional channel 5 is fixed in position relative to the distribution channel 2 in the radial direction, i.e. it cannot be moved along. It may possibly be rotatable about its longitudinal axis A5, although this is not necessary. In this solution, irrespective of the fill level of the drum 61, both the top layer of the product 56 flowing back in the radially inner region and the bottom layer of the product 56 carried upwards at the inner wall of the drum 61 are exposed to a drying gas over a large surface area. The layer thickness of the product 56 flowing over the functional channel 5 varies and is dependent on the fill level. It is possible, although not shown here, for the functional channel to be movable or displaceable relative to the rotation axis of the drum 61 or the distribution channel 2 in the radial direction.

Figure 3B:
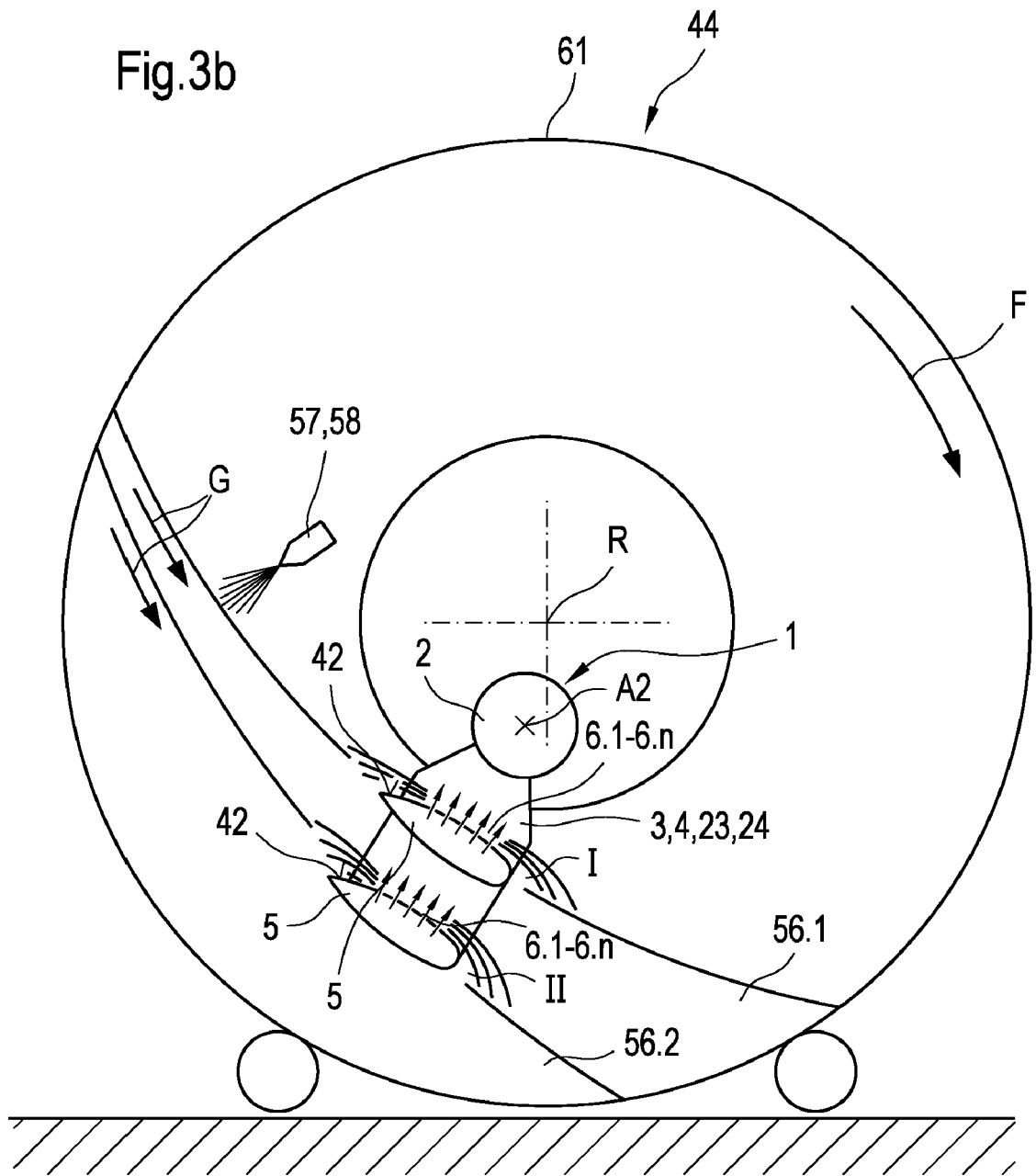

By contrast FIG. 3b shows another embodiment with an adjustable functional channel 5, as shown by way of example in FIGS. 1c and 2. The functional channel 5 has outlet openings 6.1 to 6.n only on its side directed towards the distribution channel 2, especially the upper surface 42. The functional channel 5 is movable parallel to the longitudinal axes A3, A4 of the connection channels 3, 4 thereon. FIG. 3b illustrates the situations with different fill levels. 56.1 shows a maximum fill level at which the functional channel 5 is arranged in functional position I or is moved into this position. 56.2 shows the layer thickness of the product at the minimum fill level. The functional channel 5 is then in functional position II. Thanks to the vertical adjustment of the functional channel 5 and preferably its additional rotatability the functional channel 5 is able to equalise an increase in volume and the product 56 always flows over the functional channel 5 in the same layer thickness in each of the functional positions I and II and the positions situated between them. The adjustment may take place actively during the treatment process as the fill level changes or may be carried out before filling.

FIGS. 4a to 4c show possible arrangements of the outlets 6.1 to 6.n on the functional channel 5 and embodiments of the functional channel 5, by way of example.

FIG. 4a shows an embodiment of a tongue 38 with outlets 6.1 to 6.n arranged only on the surface zones 42 that form the top.

FIG. 4b shows an embodiment of the tongue 38 that forms the functional channel 5 with outlets 6.1 to 6.n arranged on the surfaces 42, 43 that form the top and bottom.

In both embodiments, the outlets 6.1 to 6.n are preferably arranged over the entire extent of the functional channel 5 in the longitudinal direction, i.e. along the longitudinal axis A5.

By contrast, FIG. 4c shows another embodiment of a tongue 38 carrying or forming the functional channel 5, which is of telescopic design and thus is adjustable in length. For this purpose the tongue 38 is made in at least two sections, the individual sections 38.1, 38.2 being movable relative to one another, the section 38.1 being at least partly slidable into 38.2. The two sections 38.1 and 38.2 are made to different sizes in the sliding region for this purpose. The connection between them is also substantially airtight. The outlets 6.1 to 6.n are concentrated in a plurality of surface zones 59 and 60, in this case two, by way of example. These may be releasably connected to the base element that forms the functional channel 5, and then, when there is total overlap after pushing together, the surface zone 59 of the element 59 that is then on the inside is removed and the exit then takes place solely over the surface zone 60.

FIG. 5 shows in a schematically simplified representation the basic structure of an installation 1' according to the invention for use in apparatus for treating granular products by drying, film-coating or coating, especially for apparatus for treating pharmaceutical particles according to the second proposed solution. This comprises a central distribution channel 2 that can be connected to an incoming air supply unit (not shown here) when installed in the above-mentioned apparatus and from which a connection channel 3 extends at an angle α1, preferably 90°. A convergence channel is provided that acts as an actual functional channel 5 in the form of the outlet channel, which is spaced from the distribution channel 2 and connected to the connection channel 3. It comprises an inlet region 11 and a plurality of outlet openings 6.1 to 6.n for the incoming air entering it through the channel 3. This ensures that air can escape over a larger surface area. A number of basic alternatives can be differentiated, according to the arrangement and coupling of the individual channels to one another. All the variants may be configured with a fixed relationship with regard to the position between the distribution channel 2 and the functional channel 5 or a variable relationship. Changes in the relationship are essentially characterised by the possible rotation of the functional channel 5 about its axis A5, especially the mounting axis and/or its linear movement relative to the distribution channel 2, altering the spacing h in the vertical direction to the distribution channel 2. In all the embodiments there are no restrictions as to the cross-sectional geometry adopted for the individual channels, especially the connection channel 3 and the distribution channel 2 and functional channel 5. In the example illustrated, the functional channel 5 extends away from the connection channel 3 and is preferably mounted in an overhung position thereon. It would also be possible to couple the connection channel 3 to the functional channel 5 in the centre. There is then a reversal of flow or at least a deflection between the distribution channel and the outlets 6.n. The functional channel 5 may be fixedly mounted relative to the distribution channel 2 or its position relative to the distribution channel 2 may be altered by the possible methods already described in the previous Figures, i.e. adjusted in height and/or rotated.

All the embodiments described are examples that do not restrict the scope of protection. The possible embodiments of the individual elements may also be combined with one another.

What is claimed is:

1. An installation for guiding a gas for an apparatus for treating granular products by drying, film-coating or coating, comprising:
   a central distribution channel for receiving a supply of gas and including axially spaced outlets for the gas that are spaced apart along the central distribution channel,
   respective connection channels, each connected at one end to a respective one of the axially spaced outlets such that the connection channels operate to receive the gas from the central distribution channel, and
   a functional channel comprising: (i) at least two inlet regions axially spaced from one another, each of the inlet regions being connected to a respective one of the connection channels such that the functional channel operates to receive the gas from the connection channels; and (ii) a plurality of outlet openings arranged between the two inlet regions, viewed in an axial direction of the functional channel, the plurality of outlet openings operating to permit the gas to escape from the functional channel,
   wherein the functional channel in one or more inlet regions is mounted in a slide which is guided on the elements that form the connection channels in a guide, while in every position of the slide relative to the guide the functional channel is connected in flow-carrying manner to the distribution channel.

2. The installation according to claim 1, wherein at least one of the connection channels and the functional channel are arranged at an angle to one another.

3. The installation according to claim 1, wherein the functional channel is mounted in an overhung position to the connection channels.

4. The installation according to claim 1, wherein the outlet openings are arranged at least on a part of an outer surface of the functional channel facing the central distribution channel.

5. The installation according to claim 1, wherein the outlet openings are arranged on a part of an outer surface of the functional channel directed away from the central distribution channel.

6. The installation according to claim 1, wherein the outlet openings cover at least one predefined surface zone on an outer periphery of the functional channel.

7. The installation according to claim 6, wherein each outlet opening includes an outlet cross section with dimensions in the range from 0.1 to 1 mm, and each outlet opening is arranged at a predefined spacing in the range from 0.5 to 2 mm from one another in the axial direction and perpendicularly thereto.

8. The installation according to claim 1, wherein the outlet openings, viewed in the axial direction, are arranged at least over part of an axial extent of the functional channel.

9. The installation according to claim 1, wherein the central distribution channel and the functional channel are arranged parallel to one another.

10. The installation according to claim 1, wherein the central distribution channel and the functional channel are arranged at an angle to one another.

11. The installation according to claim 1, wherein the central distribution channel and at least one of the connection channels are arranged perpendicularly to one another.

12. The installation according to claim 1, wherein the functional channel and at least one of the connection channels are arranged perpendicularly to one another.

13. The installation according to claim 1, wherein the central distribution channel, the functional channel and at least one of the connection channels each have any desired cross-sectional geometry.

14. The installation according to claim 1, wherein the functional channel is wing-like, viewed in cross-section, and is formed by a top side and a bottom side joined together by rounded transitions, the top and bottom sides, viewed in cross-section, each having a side-by-side arrangement of differently configured and aligned surface zones.

15. The installation according to claim 14, wherein the functional channel is symmetrically constructed in cross-section relative to a plane.

16. The installation according to claim 1, wherein the functional channel is variable in its position relative to the central distribution channel.

17. The installation according to claim 16, wherein the functional channel is rotatable about its longitudinal axis.

18. The installation according to one of claim 16, wherein the functional channel is movable parallel to the individual connection channel or connection channels.

19. The installation according to claim 16, wherein at least one positioning device is associated with the functional channel for changing position, the positioning device operating according to mechanical principles.

20. The installation according to claim 19, wherein the positioning device is integrated in the central distribution channel and one or more of the connection channels.

21. The installation according to claim 19, wherein the positioning device is arranged outside the central distribution channel and one or more of the connection channels.

22. The installation according to claim 1, wherein at least one of the connection channels is invariable in its length.

23. The installation according to claim 1, wherein at least one of the connection channels is of telescopic construction.

24. The installation according to claim 1, further comprising an actuating device for the functional channel on which a desired value for a variable that at least indirectly characterises at least one of: (i) a displacement distance s, and (ii) a rotation angle, is preset, and which is connected to a transmission unit that converts the desired value into a set value.

25. The installation according to claim 24, wherein the transmission unit comprises a gear that converts a rotary movement into a longitudinal movement.

26. The installation according to claim 1, wherein the functional channel is of telescopic construction.

27. The installation according to claim 1, wherein at least one of the connection channels is formed by an element that forms a hollow body, which is connected to the central distribution channel through an opening area in a flow-carrying connection, and extends away from the central distribution channel.

28. The installation according to claim 1, wherein the functional channel is formed by an element that forms a hollow body, the outer periphery of which has a surface containing at least one opening formed therein.

29. The installation according to claim 28, wherein the hollow body that forms the functional channel is formed at least partly of a perforated metal sheet with a support structure or a perforated metal foil.

30. The installation according to claim 1, wherein the elements forming the central distribution channel, the functional channel and the connection channels are made of metal, plastics or inert material.

31. The installation according to claim 30, wherein the elements that form or carry the central distribution channel, the functional channel and the connection channels are made from stainless steel components which are joined together releasably or non-releasably.

32. The installation according to claim 1, wherein the functional channel is sectional and surface zones that form the outlets are releasably connected to a base element that forms the functional channel.

33. An apparatus for treating granular products by drying, film-coating or coating, having a drum mounted to be rotatable about an axis and adapted to be filled with the product, having an installation mounted in the drum for guiding a gas according to claim 1.

34. The apparatus according to claim 33, wherein the functional channel is arranged parallel to the rotation axis (R) of the drum.

35. The according to claim 33, wherein upstream of the installation is arranged an installation for applying medium.

36. An installation for guiding a gas for an apparatus for treating granular products by drying, film-coating or coating, comprising:
a central distribution channel for receiving a supply of gas and including axially spaced outlets for the gas that are spaced apart along the central distribution channel,
respective connection channels, each connected at one end to a respective one of the axially spaced outlets such that the connection channels operate to receive the gas from the central distribution channel,
a functional channel comprising: (i) at least two inlet regions axially spaced from one another, each of the inlet regions being connected to a respective one of the connection channels such that the functional channel operates to receive the gas from the connection channels; and (ii) a plurality of outlet openings arranged between the two inlet regions, viewed in an axial direction of the functional channel, the plurality of outlet openings operating to permit the gas to escape from the functional channel, and an actuating device for the functional channel on which a desired value for a variable that at least indirectly characterises at least one of: (i) a displacement distance s, and (ii) a rotation angle, is preset, and which is connected to a transmission unit that converts the desired value into a set value.

37. The installation according to claim 36, wherein the transmission unit comprises a gear that converts a rotary movement into a longitudinal movement.

38. The installation according to claim 36, wherein at least one of:

the outlet openings, viewed in the axial direction, are arranged at least over part of an axial extent of the functional channel;

the central distribution channel and the functional channel are arranged parallel to one another;

the central distribution channel and the functional channel are arranged at an angle to one another;

the central distribution channel and at least one of the connection channels are arranged perpendicularly to one another; and the functional channel and at least one of the connection channels are arranged perpendicularly to one another.

39. The installation according to claim 36, wherein at least one of:

the functional channel is wing-like, viewed in cross-section, and is formed by a top side and a bottom side joined together by rounded transitions, the top and bottom sides, viewed in cross-section, each having a side-by-side arrangement of differently configured and aligned surface zones;

the functional channel is symmetrically constructed in cross-section relative to a plane;

the functional channel is variable in its position relative to the central distribution channel;

the functional channel is rotatable about its longitudinal axis; and the functional channel is movable parallel to the individual connection channel or connection channels.

* * * * *